(12) United States Patent
Rick

(10) Patent No.: US 10,309,808 B2
(45) Date of Patent: Jun. 4, 2019

(54) FLUID QUANTIFICATION INSTRUMENT AND METHOD

(71) Applicant: Hach Company, Loveland, CO (US)

(72) Inventor: David Langley Rick, Longmont, CO (US)

(73) Assignee: HACH COMPANY, Loveland, CO (US)

( * ) Notice: Subject to any disclaimer, the term of this patent is extended or adjusted under 35 U.S.C. 154(b) by 394 days.

(21) Appl. No.: 14/841,079

(22) Filed: Aug. 31, 2015

(65) Prior Publication Data

US 2015/0369641 A1     Dec. 24, 2015

Related U.S. Application Data

(60) Continuation of application No. 14/661,906, filed on Mar. 18, 2015, now Pat. No. 9,927,268, which is a division of application No. 13/459,561, filed on Apr. 30, 2012, now Pat. No. 8,999,139, which is a continuation-in-part of application No. PCT/US2011/038124, filed on May 26, 2011.

(51) Int. Cl.
*G01F 1/00* (2006.01)
*G01N 33/18* (2006.01)
*G01N 27/416* (2006.01)

(52) U.S. Cl.
CPC ........ *G01F 1/002* (2013.01); *G01N 27/4167* (2013.01); *G01N 27/4168* (2013.01); *G01N 33/182* (2013.01); *Y10T 436/115831* (2015.01); *Y10T 436/12* (2015.01)

(58) Field of Classification Search
CPC combination set(s) only.
See application file for complete search history.

(56) References Cited

U.S. PATENT DOCUMENTS

2012/0004755 A1* 1/2012 Noll ................ C12M 21/12
                                                             700/104
2017/0205266 A1* 7/2017 Le Gonidec ........... G01F 9/001

FOREIGN PATENT DOCUMENTS

EP       2000754 A2 * 12/2008 ............ F25B 25/005
JP       11023727 A  * 1/1999

OTHER PUBLICATIONS

Over Haukenes et al, Using NMPC Based on a Low-Order Model for Controlling Pressure During Oil Well Drilling, 2007.*
Of Ko et al, . GP-UKF: Unscented Kalman Filters with Gaussian Process Prediction and Observation Models, 2007.*

* cited by examiner

*Primary Examiner* — Mamadou L Diallo
(74) *Attorney, Agent, or Firm* — Ference & Associates LLC

(57) ABSTRACT

A fluid quantification instrument is provided according to the invention. The fluid quantification instrument includes one or more sensor probes and meter electronics in communication with the one or more sensor probes. The meter electronics are configured to receive one or more raw fluid measurements from the one or more sensor probes, process the one or more raw fluid measurements using a predictive system model to produce one or more optimized fluid measurements, and determine one or more fluid quantifications using at least the one or more optimized fluid measurements.

20 Claims, 10 Drawing Sheets

FIG. 6

FLUID QUANTIFICATION INSTRUMENT AND METHOD

CROSS REFERENCE TO RELATED APPLICATIONS

This application is a continuation application of U.S. patent application Ser. No. 14/661,906, filed on Mar. 18, 2015, which in turn is a divisional application of U.S. patent application Ser. No. 13/459,561, filed on Apr. 30, 2012, which is a continuation-in-part of PCT/US11/38124, filed on May 26, 2011; each prior application is incorporated by reference herein.

BACKGROUND OF THE INVENTION

1. Field of the Invention

The invention is related to the field of fluid quantification, and in particular, to fluid quantification including fluid flow quantification.

2. Statement of the Problem

Water flow measurement is typically required for municipalities, including measuring run-off water or water in storm drains or sewers. However, the amount of flow can be varying and at times can be unpredictable. Because normal wastewater flows may be added to by storms or other unexpected or uncontrolled events, sewer pipes or sewer systems typically are constructed to be large enough to handle most excessive flow events. Consequently, wastewater conduits are partially filled and act as open channels, absent an unexpectedly high fluid collection. The flow depth typically is only a fraction of the conduit depth most of the time.

Measuring the flow rate of a fluid in an open conduit poses some challenges. The flow rate may vary significantly according to factors such as the slope of the conduit, the roughness of the conduit, the presence of any obstructions and/or changes in direction of the conduit, the nature of the fluid and the viscosity and presence of solid objects or particulate matter in the fluid, and any other interactions between the fluid and the conduit. In addition, the flow depth will play an important part in the flow rate, wherein changes in flow depth will affect the flow velocity, turbulence in the flow, likelihood of obstructions of the flow, etc. Further, a velocity sensor may have dropouts during low flow conditions. For example, a submerged Doppler velocity probe may have dropouts due to insufficient particulates (targets) or the sensor not being submerged.

A flow meter for an open channel flow typically performs a fluid depth measurement (d) and a fluid velocity measurement (v), where the fluid flow rate f is defined as f=(v)(A), where the cross-sectional area (A) may vary with the flow depth (d). The depth (d) is therefore used to determine the area (A). Depending on the instrument, one or more depth probes and one or more velocity probes may be employed. Redundant sensors can be included in order to increase or maintain accuracy.

Depth measurement in an open channel is relatively easy to accomplish. One approach is a pressure measurement, wherein a fluid pressure can be correlated to a fluid depth. Other depth measurements can also be employed, such as an ultrasonic or electromagnetic measurement that directly determines a fluid depth or that indirectly determines fluid depth by determining the distance to the fluid surface.

One type of fluid flow velocity measurement is a measurement of the velocity of the fluid surface. Advantageously, such measurement can be performed non-intrusively, such as from a probe above the fluid surface. For example, the velocity sensor can be located at the top of the conduit or channel and can direct a measurement beam or beams downward onto the fluid surface.

However, measurement of the fluid surface velocity can have difficulties. Objects on the surface can give false readings and can be moving at different velocities than the fluid. For example, the fluid surface can include ripples or waves, solid objects, solid objects that are trapped or hung up (i.e., tree branches, trash, etc.) and can produce noisy or inaccurate readings.

Another type of fluid flow velocity measurement utilizes a submerged ultrasonic probe to make velocity measurements based on Doppler or correlation techniques. Such probes measure the movement of large ensembles of particles carried within the flowing fluid. The resulting velocity measurements may thus better represent the average velocity of the fluid over the channel cross-section.

The potentially better accuracy of submerged probes is balanced by greater difficulties in their use. Because such probes are submerged in a flow which may include high particulate loads, sewage, and corrosive industrial discharges, they may experience degraded function or outright failure due to silting, fouling, and corrosion. These problems sometimes result in velocity measurements which are noisy, inaccurate, or completely missing.

Consequently, a fluid flow rate produced from the fluid velocity measurement will be affected by any inaccuracies or gaps in the fluid velocity measurement.

SUMMARY OF THE INVENTION

In one aspect of the invention, a fluid quantification instrument is provided. The fluid quantification instrument comprises:
  one or more sensor probes; and
  meter electronics in communication with the one or more sensor probes, with
  the meter electronics being configured to receive one or more raw fluid measurements from the one or more sensor probes, process the one or more raw fluid measurements using a predictive system model to produce one or more optimized fluid measurements, and determine one or more fluid quantifications using at least the one or more optimized fluid measurements Preferably, the predictive system model is provided by an unscented Kalman filter.

Preferably, the one or more raw fluid measurements including at least a raw fluid depth measurement signal and a raw fluid velocity measurement signal that are used to determine a volume flow rate of the fluid.

Preferably, the meter electronics being further configured to generate a plurality of Fourier coefficients related to a flow state periodicity.

Preferably, the meter electronics being further configured to generate a plurality of Fourier coefficients related to a periodicity in one or more elements of a state vector.

Preferably, further comprising comparing one or more elements of the predictive system model to one or more corresponding thresholds and performing one or more optimization actions if the one or more elements do not satisfy the one or more corresponding thresholds.

Preferably, the one or more elements of the predictive system model comprising a predicted measurement error $|(y_k - \hat{y}_k^-)|$ that is compared to predetermined scaled elements of the sensor covariance matrix $(P_y)$, an estimated measurement error $|(y_k - \hat{y}_k^+)|$ that is compared to predetermined scaled elements of the sensor covariance matrix ($P_y$), or an estimated state error $|(\hat{x}_k^+ - \hat{x}_k^-)|$ that is compared to predetermined scaled elements of the state covariance matrix ($P_x$).

Preferably, performing one or more optimization actions comprising decreasing a measurement interval if the one or more elements of the predictive system model do not satisfy the one or more corresponding thresholds.

Preferably, performing one or more optimization actions comprising determining a future timing of one or more predetermined raw measurements based on the one or more elements of the predictive system model or selecting one or more predetermined sensors to use based on the one or more elements of the predictive system model in order to affect power consumption of the fluid quantification instrument.

Preferably, a predetermined optimized fluid measurement is obtained by combining two or more predetermined raw fluid measurements through statistical sensor fusion.

In one aspect of the invention, a fluid quantification method is provided. The fluid quantification method comprises:
   receiving one or more raw fluid measurements;
   processing the one or more raw fluid measurements using a predictive system model to produce one or more optimized fluid measurements; and
   determining one or more fluid quantifications using at least the one or more optimized fluid measurements.

Preferably, the predictive system model is provided by an unscented Kalman filter.

Preferably, the one or more raw fluid measurements including at least a raw fluid depth measurement signal and a raw fluid velocity measurement signal that are used to determine a volume flow rate of the fluid flow.

Preferably, further comprising generating a plurality of Fourier coefficients related to a flow state periodicity.

Preferably, further comprising generating a plurality of Fourier coefficients related to a periodicity in one or more elements of a state vector.

Preferably, further comprising comparing one or more elements of the predictive system model to one or more corresponding thresholds and performing one or more optimization actions if the one or more elements do not satisfy the one or more corresponding thresholds.

Preferably, the one or more elements of the predictive system model comprising a predicted measurement error $|(y_k - \hat{y}_k^-)|$ that is compared to predetermined scaled elements of the sensor covariance matrix ($P_y$), an estimated measurement error $|(y_k - \hat{y}_k^+)|$ that is compared to predetermined scaled elements of the sensor covariance matrix ($P_y$), or an estimated state error $|(\hat{x}_k^+ - \hat{y}_k^-)|$ that is compared to predetermined scaled elements of the state covariance matrix ($P_x$).

Preferably, performing one or more optimization actions comprising decreasing a measurement interval if the one or more elements of the predictive system model do not satisfy the one or more corresponding thresholds.

Preferably, performing one or more optimization actions comprising determining a future timing of one or more predetermined raw measurements based on the one or more elements of the predictive system model or selecting one or more predetermined sensors to use based on the one or more elements of the predictive system model in order to affect power consumption.

Preferably, a predetermined optimized fluid measurement is obtained by combining two or more predetermined raw measurements through statistical sensor fusion.

DESCRIPTION OF THE DRAWINGS

The same reference number represents the same element on all drawings. It should be understood that the drawings are not necessarily to scale.

Figure 6:
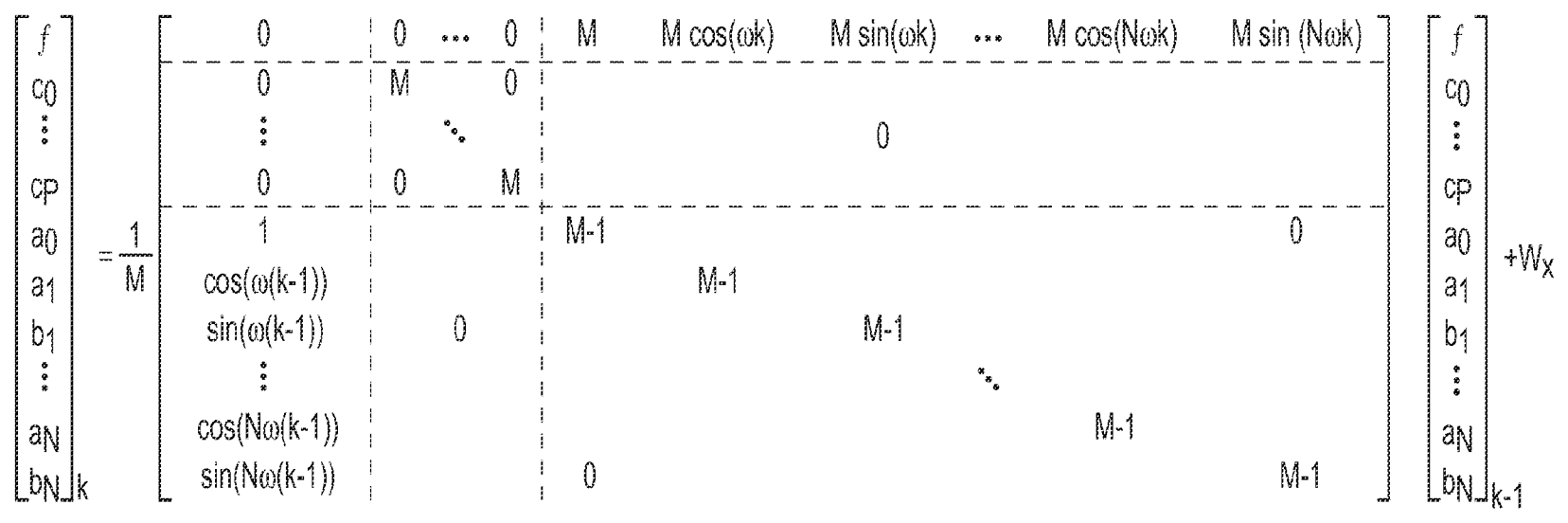

FIG. 6 shows a complete state transition model according to an embodiment of the invention.

DETAILED DESCRIPTION OF THE INVENTION

FIGS. 1-10 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 1:
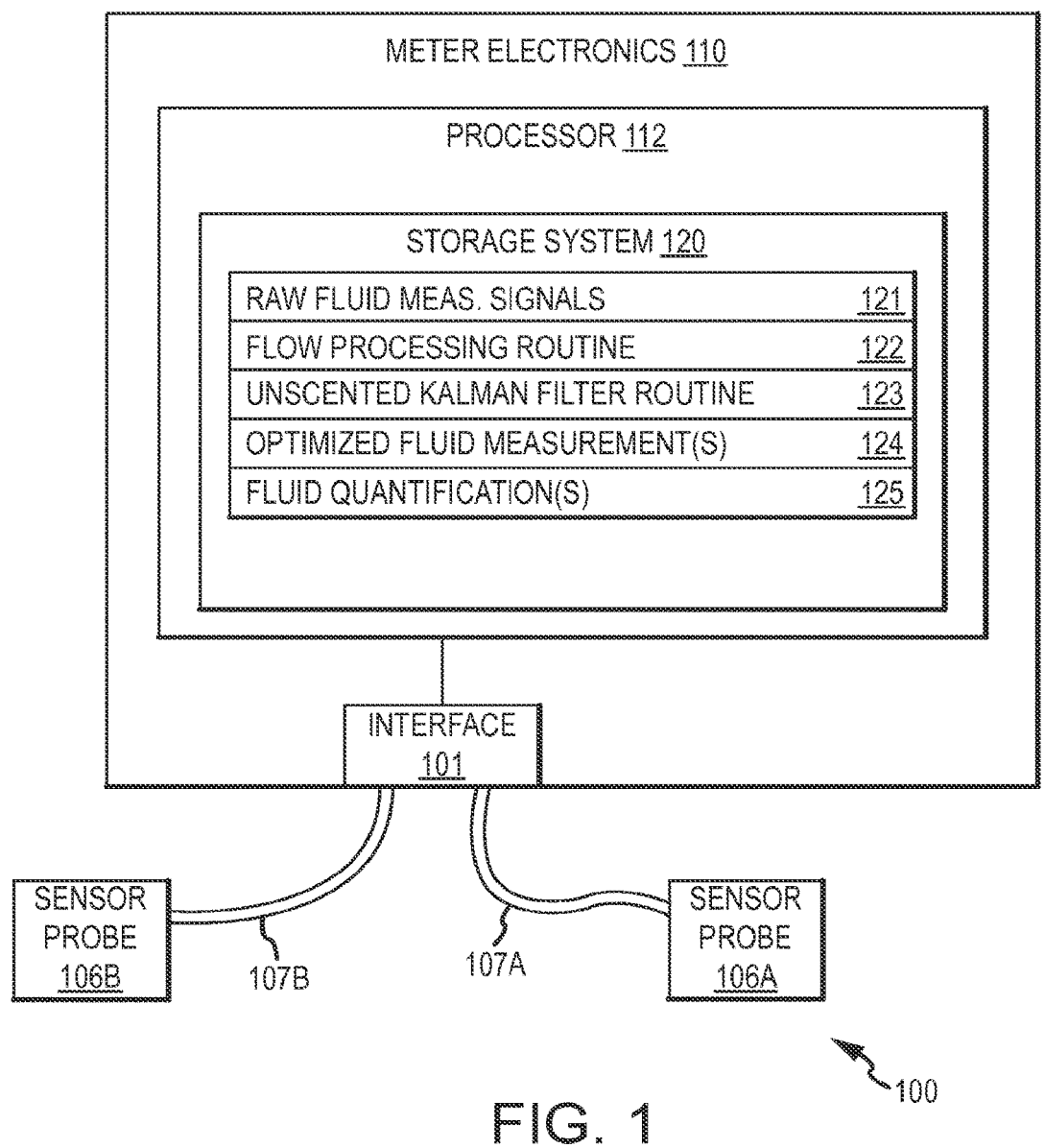
FIG. 1 shows a fluid quantification instrument according to an embodiment of the invention.

FIG. 1 shows a fluid quantification instrument 100 according to an embodiment of the invention. The fluid quantification instrument 100 includes a meter electronics 110 and one or more probes 106A-106B coupled to the meter electronics 110 via one or more corresponding cables 107A-107B or other signal transmission apparatus. The one or more probes 106A-106B can comprise various types of probes that measure various flow characteristics. It should be understood that the one or more probes 106A-106B can include duplicate probes that provide substantially redundant data, for example.

The one or more probes 106A-106B can measure various characteristics of water or a water flow and generate one or more raw fluid measurements. Alternatively, the one or more probes 106A-106B can be used for various other fluids. The one or more probes 106A-106B can measure fluid characteristics that are manipulated, combined, or otherwise processed to generate one or more fluid characteristics that are not directly obtained.

Some instruments can measure the fluid flow rate directly, such as through use of a rotating turbine, for example. However, such instruments require intrusion into the fluid flow and therefore are often vulnerable to plugging or obstruction by solid objects in the flow.

The fluid quantification instrument 100 in some embodiments comprises a non-intrusive instrument, wherein electromagnetic or acoustic waves interact with the fluid being measured. Alternatively, the fluid quantification instrument 100 can include intrusive probes or measurement devices.

The one or more raw fluid measurements may be processed substantially in real time. Alternatively, the one or more raw fluid measurements may be processed substantially after the one or more raw fluid measurements are generated.

In some embodiments, the meter electronics 110 is remotely located from the one or more sensor probes 106, such as in a monitoring station, data accumulation station, server, et cetera. The meter electronics 110 may be in communication with one or more sets of the one or more sensor probes 106.

The fluid quantification instrument 100 can be used to measure various fluid flow characteristics. The fluid quantification instrument 100 advantageously can be used to generate optimized measurements where the end flow characteristics are not directly determined but are obtained from a processing or combination of other measurements. For example, the fluid quantification instrument 100 can generate a fluid volume flow rate quantification, wherein the volume flow rate is not directly measured and instead is non-invasively measured through a combination of flow depth and flow velocity measurements.

One application is in generating a volume flow rate of fluid flow in a channel. The water can be flowing in an open channel or in a closed channel. Measurement of a flow in an open channel typically poses more of a challenge than measurement of a flow in a closed channel, as the flow rate will vary based on the level of fill in the channel. The rate is affected by the level of fluid, the surface of the channel, channel slope, fluid type, objects or obstructions in the fluid, etc.

Figure 2:
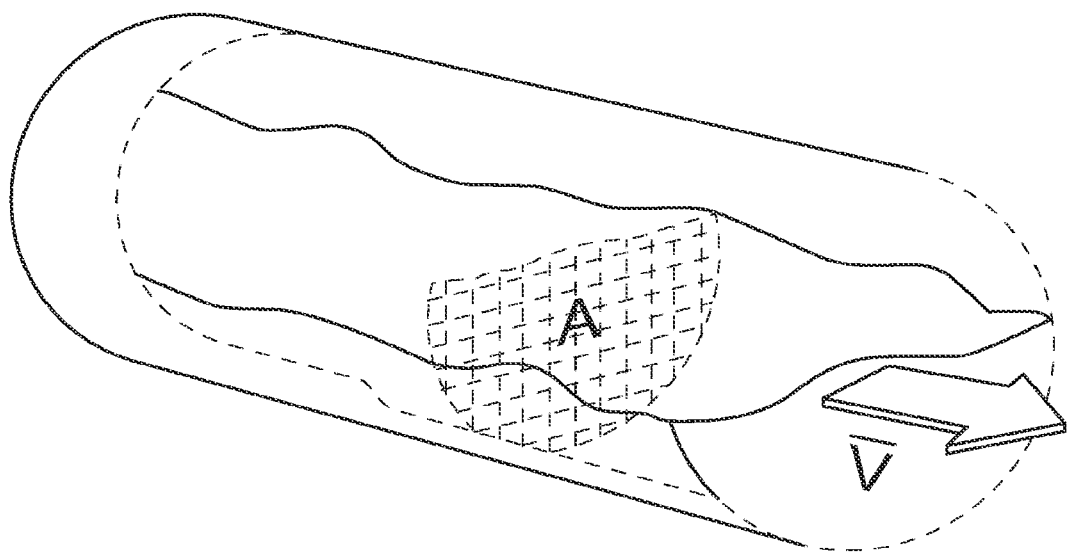
FIG. 2 illustrates a volume flow rate determination method.

FIG. 2 illustrates a volume flow rate determination method. The volume flow rate f is indirectly determined in this example. The volume flow rate (f) is derived by multiplying the fluid velocity (v) by the cross-sectional channel area (A). The area (A) is dependent on and is determined from the fluid depth. The velocity (v) can be an average velocity ($\bar{v}$), for example, or can be further processed in order to derive a substantially average fluid velocity from the measured velocity (v). Consequently, the volume flow rate (f) can be determined from measurements of flow depth and flow velocity.

Figure 3:
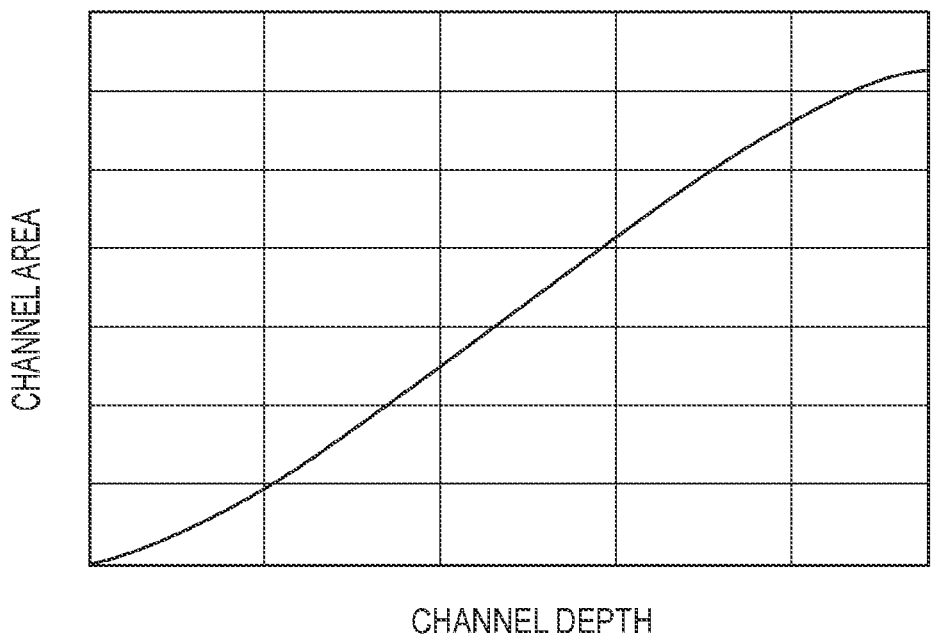
FIG. 3 is a graph of flow cross-sectional area versus flow depth for a typical open channel fluid conduit.

FIG. 3 is a graph of flow cross-sectional area versus flow depth for a typical open channel fluid conduit. The graph reflects the configuration of the open channel fluid conduit and can vary according to the cross-sectional shape of the conduit. It can be seen that the cross-sectional area of the conduit may not necessarily be linearly related to the flow depth, depending on the cross-sectional shape. The non-linearity makes predictions of flow depth more difficult.

Figure 4:
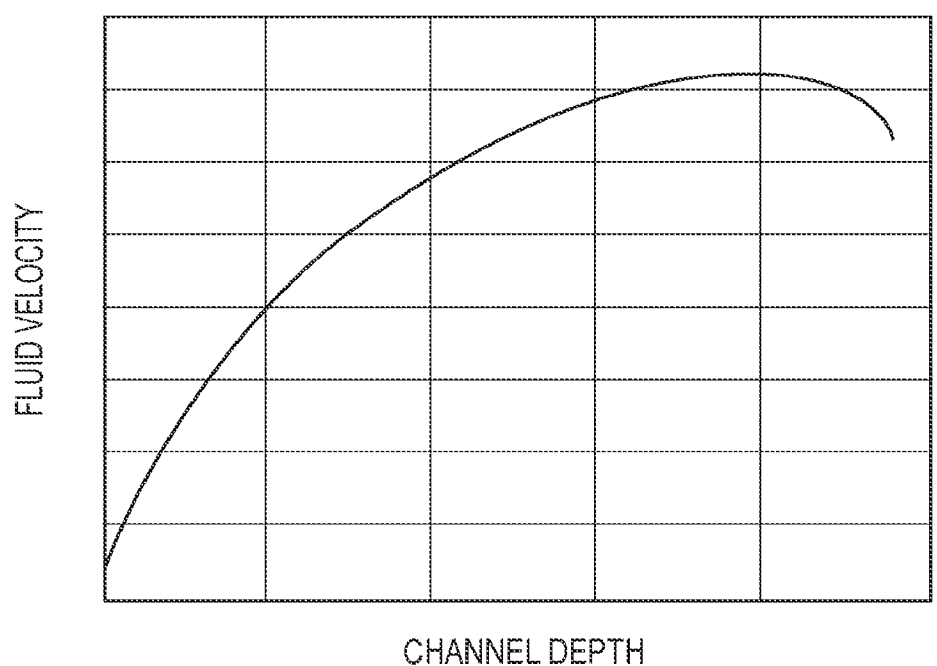
FIG. 4 is a graph of flow velocity versus flow depth for a typical open channel fluid conduit.

FIG. 4 is a graph of flow velocity versus flow depth for a typical open channel fluid conduit. The graph reflects a non-linearity in the flow velocity over changes in flow depth. The non-linearity makes predictions of flow velocity more difficult.

Referring again to FIG. 1, the flow velocity can be measured by measuring a Doppler frequency shift in waves reflected from moving targets, whether from within the fluid, or at the fluid surface. The targets may be waves, ripples, or other disturbances on the surface or they may be particles, objects, or fluid or other phase boundaries in the fluid flow. The waves can comprise any manner of suitable waves, including acoustic and electromagnetic waves. However, the Doppler shift can be affected by various extraneous factors, including noise, unwanted reflections, turbulence in the fluid flow, blockages, etc. As a result, the flow velocity measurement may be subject to spikes, drop-outs, or other anomalies in the measurement, and these can carry through to a volume flow rate determination. Such measurement anomalies can have significant effect on the accuracy and reliability of the measurements.

The drawback is that any error in either fluid measurement (depth or velocity) will invariably affect the resulting flow rate calculation. To this end, the fluid quantification instrument 100 employs an unscented Kalman filter in processing measurement data. The unscented Kalman filter is also referred to as a sigma point Kalman filter. The unscented Kalman filter enables a reduction in noise in the measurement signals, providing a measurement of increased quality. The unscented Kalman filter also can provide prediction of measurement data, wherein the predicted measurement data can serve as a substitute or gap-filler in the actual measurement data. For example, the predicted measurement data can fill in when the measurement signal drops out. Moreover, the predicted measurement data can be augmented with information gleaned from other sensors to more accurately replace the missing data. The unscented Kalman filter may be used in order to handle any non-linearity of the level and/or velocity sensors.

The Kalman filter is an efficient recursive filter that estimates the state of a process or system from a series of incomplete and noisy measurements. However, the conventional Kalman filter models a process or system as being essentially linear. Therefore, if the initial estimate of the state is wrong, or if the process is modeled incorrectly, the filter may quickly diverge, owing to its linearisation. This is due to the propagation of mean and variance values through the non-linearity. The original Kalman filter is therefore unsatisfactory in many applications.

As a result, the unscented Kalman filter was subsequently developed. The unscented Kalman filter uses a deterministic sampling technique known as the unscented transform to pick a set of sample points (or "sigma points") around the mean. For this reason, the unscented Kalman filter is also known as a sigma point filter. These sigma points are then propagated through the non-linear functions and the mean and covariance of the non-linear output is then recovered. The result is a filter which more accurately captures the true mean and covariance of those variables which describe the fluid process or system.

The meter electronics 110 includes an interface 101 and a processor 112 coupled to the interface 101. The interface 101 is configured to receive the corresponding one or more raw fluid measurements from the one or more sensor probes 106A-106B and relay the signals to the processor 112. In addition, the interface 101 can perform any manner of pre-processing operations, such as digitizing the one or more raw fluid measurements, for example. The interface 101 can further perform any manner of pre-amplification or pre-filtering, as desired. Alternatively, the amplification or other pre-processing can be performed in the probe 106.

The processor 112 in some embodiments is configured to receive the one or more raw fluid measurements from the interface 101, process the one or more raw fluid measurements using a predictive system model to produce one or more optimized fluid measurements, and determine one or more fluid quantifications using at least the one or more optimized fluid measurements. The predictive system model can be provided by an unscented Kalman filter, for example. The processing system can employ the unscented Kalman filter for smoothing and improving at least some of the one or more raw fluid measurements, as will be discussed below.

The one or more raw fluid measurements are used to update a state estimate and a covariance matrix. The one or more raw fluid measurements are sequentially generated according to a predetermined update sequence. The one or more raw fluid measurements include at least a raw fluid depth measurement signal and a raw fluid velocity measurement signal that can be used to determine a volume flow rate of the fluid.

The meter electronics 110 may be further configured to generate a plurality of Fourier coefficients related to a flow state periodicity. The meter electronics 110 may be further configured to generate a plurality of Fourier coefficients related to a periodicity in one or more elements of a state vector.

The meter electronics 110 may be further configured to compare one or more elements of the predictive system model to one or more corresponding thresholds and perform one or more optimization actions if the one or more elements do not satisfy the one or more corresponding thresholds.

The one or more elements of the predictive system model can comprise a predicted measurement error vector $|(\underline{y}_k - \hat{\underline{y}}_k^-)|$ that is compared to predetermined scaled elements of the sensor covariance matrix $\underline{P}_y$. The one or more elements of the predictive system model can comprise an estimated measurement error vector $|(\underline{y}_k - \hat{\underline{y}}_k^+)|$ that is compared to predetermined scaled elements of the sensor covariance matrix $\underline{P}_y$. The one or more elements of the predictive system model can comprise an estimated state error vector $|(\hat{\underline{x}}_k^+ - \hat{\underline{x}}_k^-)|$ that is compared to predetermined scaled elements of the state covariance matrix $\underline{P}_x$. Typically, the comparison is to a vector composed of diagonal entries of the chosen covariance matrix. The elements used in the comparison may comprise scaled diagonal elements of the chosen covariance matrix.

Performing one or more optimization actions can comprise decreasing a measurement interval if the one or more elements of the predictive system model do not satisfy the one or more corresponding thresholds. Performing one or more optimization actions can comprise determining a future timing of one or more predetermined raw measurements based on the one or more elements of the predictive system model, wherein the future timing affects a power consumption of the fluid quantification instrument 100. Performing one or more optimization actions can comprise selecting one or more predetermined sensors to use based on the one or more elements of the predictive system model, wherein the selection affects a power consumption of the fluid quantification instrument 100. Performing one or more optimization actions can comprise selecting and using one or more predetermined raw measurements and/or one or more predetermined optimized fluid measurements for determining the one or more fluid quantifications through sensor fusion. Performing one or more optimization actions can comprise operating individual sensors according to whether the one or more elements of the predictive system model satisfy the one or more corresponding thresholds. Performing one or more optimization actions can comprise measuring a flow characteristic using a lowest power consuming sensor and additionally measuring the flow characteristic using a higher power consuming sensor if the one or more elements of the predictive system model do not satisfy the one or more corresponding thresholds. Performing one or more optimization actions can comprise using non-measurement data in place of raw measurement values. The non-measurement data can comprise historical data values, predicted data values, or filtered data values. The non-measurement data can be used to replace raw measurement values, such as where the raw measurement values are determined to be outliers or are suspect data values in some way. Alternatively, the non-measurement data can be used where raw measurement values are missing, such as where a sensor has dropped out due to any manner of fault or problem.

The processing further comprises using a predictive system model, wherein the predictive system model comprises a predictive portion of the unscented Kalman filter (see equation (1) below). The predictive system model is configured to handle drop-outs in the one or more raw fluid measurements. In some embodiments, the previous state $(\underline{x}_{k-1})$ drives the predictive system model, as given in equation (1) below, but without the state noise $(\underline{w}_x)$.

The processing further comprises using a predictive system model, wherein the predictive system model expresses correlations between a set of possible sensor measurements and the system state. In some embodiments, the state transition matrix $(\underline{F})$ comprises the predictive system model, as given in equation (1) below.

The processor 112 in some embodiments is configured to receive one or more raw fluid measurements from the interface 101, process the one or more raw fluid measurements using a predictive system model to produce one or more optimized fluid measurements, and determine one or more fluid quantifications using at least the one or more optimized fluid measurements.

The one or more raw fluid measurements in some embodiments can comprise at least a raw fluid depth measurement and a raw fluid velocity measurement. The one or more fluid quantifications in some embodiments can comprise an optimized fluid depth measurement, an optimized fluid velocity measurement, and/or an optimized fluid velocity measurement.

The processor 112 in some embodiments performs sensor fusion as part of the unscented Kalman filter. Sensor fusion is the use of various multiple sensors and/or multiple measurement values in order to generate an outputted measurement. In the fluid quantification instrument 100, multiple sensor probes 106 can be used and can generate multiple raw fluid level/velocity measurements, for example. The fluid quantification instrument 100 can schedule sensors/sensor measurements, can select from raw measurements, or can weight and combine raw measurements in predetermined ratios.

If the processor 112, executing the unscented Kalman filter routine 123, decides that it already has good knowledge of the system state, then it may schedule fewer measurements. Conversely, the processor 112 can schedule more measurements if the system state is uncertain.

The storage system 120 can include one or more raw fluid measurements 121, a flow processing routine 122, an unscented Kalman filter routine 123, one or more optimized fluid measurements 124, and one or more fluid quantifications 125. The one or more raw fluid measurements 121 comprise signals received from the one or more probes 106, i.e., raw measurement data. The one or more fluid quantifications 125 comprise processed measurements or flow determinations that can be stored, transferred, or output by the fluid quantification instrument 100. The one or more fluid quantifications 125 are generated from the one or more raw fluid measurements 121 by the processor 112 when executing the flow processing routine 122 and the unscented Kalman filter routine 123. However, the one or more fluid quantifications 125 may not necessarily correspond in number to the one or more raw fluid measurements.

In the prior art, unscented Kalman filters have been used in tracking of ballistic and orbital objects, such as for determining velocity and direction of flight (see prior art U.S. Pat. No. 7,249,730 to Flippen, Jr., for example). Conventional Kalman filters have also been used to track plant dynamics in, for example, chemical manufacturing. In the prior art, the unscented Kalman filter is typically used to refine and improve velocity measurements of a solid object moving at very high speeds. Unscented Kalman filters are used in robotics. However, unscented Kalman filters have not been used in the prior art to measure characteristics of a fluid flow.

U.S. Pat. No. 6,807,494 to Schutzbach discloses using historical fluid flow data to validate new measurements and also for setting alarm thresholds. The past data history may be voluminous and the prior art discloses storing data on a server, as it is impractical to store such a volume of past data in a field-deployed apparatus. The server is separate from the computer or computers that process the measured data, and is separate from the flow sensor instruments, wherein the server merely stores historical data.

In the present patent application, past history is summarized in a compact form better suited to limited memory space. Schutzbach contemplates excluding certain data as outliers, but does not improve those data that are accepted for use in reporting. In the present patent application, all available information is combined in an optimal fashion. Various sources of data are combined in accordance with their relative reliability.

Schutzbach does not perform local processing. Schutzbach does not locally process measurement data against historical data. Schutzbach does not reduce historical data to a new form for storage and/or processing. Because Schutzbach does not perform any local processing at a flow instrument, Schutzbach cannot perform power saving processes.

Advantages of the present invention include: (1) decreased data storage because actual past history is not stored, (2) improved accuracy through use of optimal noise filtration, (3) data drop-outs are filled in, and (4) power savings are realized because unnecessary measurements are avoided.

The unscented Kalman filter routine 123 can be implemented in order to perform optimization of one or more raw fluid measurements. The unscented Kalman filter routine 123 can be configured to model a state transformation represented by:

$$\underline{x}_k = \underline{F}_{k-1}\underline{x}_{k-1} + \underline{w}_x \quad (1)$$

Where the (k) subscript denotes a next measurement time, the (k−1) subscript denotes a previous measurement time, the ($\underline{x}_k$) term represents a next state of the system, the ($\underline{F}_{k-1}$) term comprises a state transition matrix, the ($\underline{x}_{k-1}$) term represents a previous (i.e., known) state, and the ($\underline{w}_x$) term represents state noise (see FIG. 6). In this model it is assumed that the noise ($\underline{w}_x$) is characterized by a covariance matrix, Q. In equations presented herein, underlined lower-case variables may be column vectors or single numbers. Underlined upper-case variables are typically matrices, but may be single numbers in particularly simple cases. Note that the unscented Kalman filter implementation does not add the noise state ($\underline{w}_x$) because the filter does not know it. Though it assumes equation (1), it actually performs ($\underline{x}_k = \underline{F}_{k-1}\underline{x}_{k-1}$). The previous state vector ($\underline{x}_{k-1}$) contains state variables and can be formed of either optimized measurements and/or other quantifications. As a result, the next state ($\underline{x}_k$) comprises the previous state ($\underline{x}_{k-1}$) multiplied by a state transition matrix ($\underline{F}_{k-1}$) plus any noise ($\underline{w}_x$) present in the measurement.

The predicted next state ($\hat{\underline{x}}_k^-$) comprises a prediction or determination of the next measurement, taken at a future time where the (k) subscript is for the next time tick after (k−1), where the (^) is for an estimated value, and where the (−) superscript indicates it is an a priori estimate of the next state. The prediction ability of the unscented Kalman filter is based on the historical data included within ($\underline{x}_{k-1}$), and the predictive system model expressed by the state transition matrix ($\underline{F}_{k-1}$). The previous state vector prediction ($\underline{x}_{k-1}$)$^-$ can include any manner of historical and/or periodicity data. The next state ($\underline{x}_k$) therefore comprises a best estimation of a next measured fluid value, based on known (i.e., historical) measurements and conditions.

The state noise ($\underline{w}_x$) term represents uncertainty and unpredictability in the state transformation. It is desired to minimize the uncertainty in the next state estimate ($\hat{\underline{x}}_k$), despite the state noise ($\underline{w}_x$). This can be accomplished through careful design and implementation of the state transition matrix, as discussed above.

The next state ($\underline{x}_k$) comprises a vector that includes several important items of information. The next state ($\underline{x}_k$) can be represented as:

$$\underline{x}_k = \begin{bmatrix} f \\ c_0 \\ \vdots \\ c_p \\ a_0 \\ a_1 \\ b_1 \\ \vdots \\ a_N \\ b_N \end{bmatrix} \quad (2)$$

Here the (f) term comprises a bulk flow measurement, the ($c_0$-$c_p$) terms comprise channel coefficients, and the ($a_0$, $a_1$, $b_1$–$a_N$, $b_N$) terms comprise Fourier coefficients. Note that the previous state vector ($\underline{x}_{k-1}$) has the same form, and contains the same items, as estimated at the previous time tick. A nominal number of channel coefficients ($c_0$-$c_p$) and Fourier coefficients ($a_0$, $a_1$, $b_1$, ... $a_N$, $b_N$) are typically required. For example, in some embodiments, a total of thirteen coefficients, including channel coefficients ($c_0$-$c_p$) and Fourier coefficients ($a_0$, $a_1$, $b_1$, ... $a_x$, $b_N$), are sufficient to generate accurate and reliable fluid quantifications.

The channel coefficients ($c_0$-$c_p$) define some aspects of the fluid flow channel. In a first embodiment, the channel coefficients ($c_0$-$c_p$) define the relationships between redundant sensors. The channel coefficients ($c_0$-$c_p$) therefore can define an offset(s) between depth sensors or correction factor(s) between velocity sensors.

In a second embodiment, the channel coefficients ($c_0$-$c_p$) define the flow channel's velocity versus depth curve (see FIG. 4). The channel coefficients ($c_0$-$c_p$) can be selected in several ways. The velocity versus depth relation can be assumed to be somewhat linear and a linear function can be chosen for a given depth. However, this is generally not an acceptably accurate technique. A more accurate representation of channel velocity versus depth comprises generating a piecewise polynomial representation based on interpolation kernels. In some embodiments, the interpolation kernels comprise B-spline kernels.

The two embodiments discussed above are not mutually exclusive. Both kinds of coefficients could be employed in some implementation embodiments.

The Fourier coefficients ($a_0, a_1, b_1, \ldots a_N, b_N$) are related to and can model a channel history, such as a channel flow history, for example. Further, the Fourier coefficients ($a_0, a_1, b_1, \ldots a_N, b_N$) can be related to and can model a flow periodicity. The channel coefficients ($c_0 \ldots c_p$) are chosen to represent a substantially non-linear flow response. The resulting Fourier coefficients ($a_0, a_1, b_1, \ldots a_N, b_N$) are more compact than storing an actual history. The Fourier prediction can be used as a Bayesian prior mean. In one embodiment, the Fourier coefficients ($a_0, a_1, b_1, \ldots a_N, b_N$) are generated using a moving average estimator.

Figure 5:
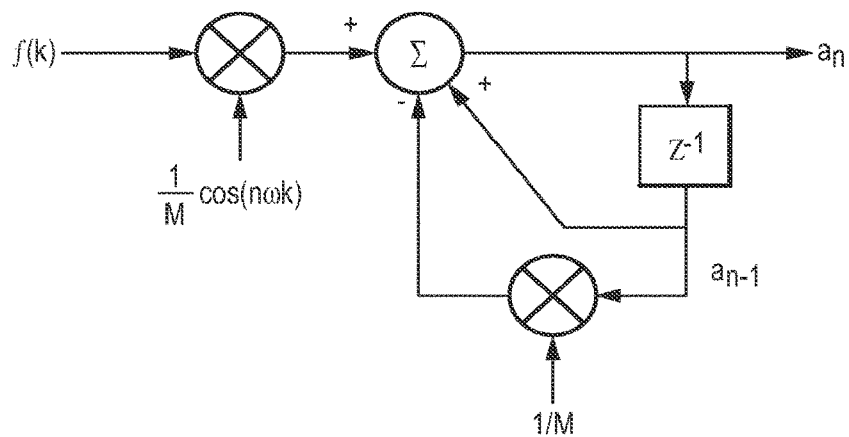
FIG. 5 shows a Fourier coefficient estimation process according to an embodiment of the invention.

FIG. 5 shows a Fourier coefficient estimation process according to an embodiment of the invention. In the first estimation element, the bulk flow measurement (f) in equation (2) is multiplied by a frequency-shift factor given as:

$$\left(\frac{1}{M}\cos(n\omega k)\right) \quad (3)$$

The frequency-shift factor includes a time or sampling factor, (1/M), where (M) determines the time constant used in the Fourier coefficient estimation. The (M) term comprises a number of time-sampled input values for an exponential averaging. In the second estimation element, the resulting frequency-shifted bulk flow measurement is summed with the output of a time delay element ($z^{-1}$). The resulting Fourier coefficient estimate is represented by:

$$a_n(k) = \frac{M-1}{M}a_n(k-1) + \frac{1}{M}f(k)\cos(n\omega k) \quad (4)$$

The equation for $b_n(k)$ is similar and involves $\sin(n\omega k)$ instead of $\cos(n\omega k)$.

FIG. 6 shows the complete state transition model of equation (1) according to an embodiment of the invention. This embodiment includes the (1/M) amplitude multiplier as part of the state transition matrix ($\underline{F}_{k-1}$). The state transition matrix multiplies the previous state vector ($\underline{x}_{k-1}$).

The unscented Kalman filter also tracks the covariance matrices $\underline{P}_x$, $\underline{P}_y$, and $\underline{P}_{xy}$. Diagonal elements of the state covariance matrix, $\underline{P}_x$, comprise variances and covariances of state variables. The measurement covariance matrix, $\underline{P}_y$, gives variances and covariances of optimized measurements. The matrix $\underline{P}_{xy}$ gives statistical relationships between elements of x and y. The variance is a statistical measure of how much a single variable varies. It can be thought of as a measure of the noise in that particular variable. Off-diagonal entries of a covariance matrix comprise the covariance between variables. Covariance is the measure of how much two random variables vary with respect to each other. Consequently, the unscented Kalman filter tracks variance and covariance, such as variance in the fluid velocity and covariance between the fluid depth and fluid velocity, in order to optimally use raw measurements and historical information. The raw fluid measurements are used to update the state estimate according to the Kalman gain, which is derived from $\underline{P}_y$ and $\underline{P}_{xy}$.

The variance and covariance give a statistical estimation of measurement and state estimate reliabilities. Changes in the variance and covariance give a statistical estimation of trends in accuracy and trends in fluid and fluid flow conditions. Moreover, changes in the variance and covariance give a statistical estimation of which fluid sensors should be trusted and used. Further, the variance and covariance give information that can lead to determinations of outliers or errors in raw measurements, wherein thresholds based upon the variance and covariance can be employed to ignore data points and/or replace or condition problematic data points, as needed.

The values in the covariance matrices $\underline{P}_x$, $\underline{P}_y$, $\underline{P}_{xy}$, and Q may be obtained in various ways. For example, an instrument may be programmed with starting values at the factory, based on known characteristics of the sensor and/or known or anticipated characteristics of the channel (i.e., information regarding intended use of the fluid quantification instrument). Alternatively, or in addition, the user may be given control of relative values (such as one sensor compared to another) and may adjust their ratios according to perception of sensor reliability, or may review produced data and revise the covariance matrices empirically, in order to make the filtered data reflect actual flows. In another alternative, the Kalman filter could be augmented with an on-line running estimator that changes covariance entries based upon observed statistics of incoming measurements. Various method exist for this, and are known to those skilled in the art.

A formula of interest is the Kalman measurement model. It augments the Kalman predictive system model, and represents how the system state manifests sensor measurements. The Kalman measurement model can be expressed as:

$$\underline{y}_k = g(\underline{x}_k, \underline{c}) + \underline{w}_y \quad (5)$$

Here the ($\underline{y}_k$) comprises a measurement vector, the g( ) function comprises a (possibly nonlinear) measurement function, the ($\underline{x}_k$) term comprises the previously discussed state vector, and the ($\underline{w}_y$) term comprises measurement noise. The measurement function, g( ), represents the idealized operation of the sensors used to generate the raw measurements, as well as the effect of the channel. The measurement function, g, may depend on the channel coefficients ($c_0, \ldots c_p$). The measurement noise ($\underline{w}_y$) comprises noise picked up and/or inherent in the measurement device, such as in the sensor probes 106, within the meter electronics 110, from nearby noise sources, etc.

The measurement vector ($\underline{y}_k$) comprises a vector that represents current raw fluid measurements. The measurement vector ($\underline{y}_k$) can be of any needed size. When the measurement vector holds information of raw fluid depth and raw fluid velocity measurements, the measurement vector ($\underline{y}_k$) can be represented as:

$$\underline{y}_k = \begin{bmatrix} d_1 \\ d_2 \\ \vdots \\ v_1 \\ v_2 \\ \vdots \end{bmatrix} \quad (6)$$

in which the ($d_1, d_2, \ldots$) terms are raw depth measurements and the ($v_1, v_2, \ldots$) terms are raw velocity measurements.

The first part of the Kalman prediction step comprises computing the ($\underline{F}_{k-1}$) matrix, i.e., the large matrix in FIG. 6. It should be noted that ($\underline{F}_{k-1}$) is a function of time. Next compute the a priori state estimate:

$$\hat{\underline{x}}_k^- = \underline{F}_{k-1}\hat{\underline{x}}_{k-1}^+ \quad (7)$$

Compute the a priori state covariance:

$$\underline{P}_x^-(k) = \underline{F}_{k-1}\underline{P}_x^+(k-1)\underline{F}_{k-1}^T + \underline{Q} \tag{8}$$

wherein, Q is a covariance matrix describing the state noise, $(\underline{w}_x)$, of (1). In the sigma point portion of the algorithm, during the update step, let α be a small number, such as 0.01, and δ=2 (correct for Gaussian noise). A matrix, $\underline{\Delta}$, is computed such that $$\underline{\Delta}\underline{\Delta}^T = \frac{N}{\alpha}\underline{P}_x^-.$$

This is a lower triangular "matrix square root", or Cholesky factor. Denote the ith column of $\underline{\Delta}$ by $\underline{\Delta}_i$, and compute 2N+1 sigma points, $\chi^{(i)}$, according to:

$$\underline{\chi}^{(i)} = \begin{cases} \hat{\underline{x}}_k^- & i = 0 \\ \hat{\underline{x}}_k^- + \underline{\Delta}_i & i = 1, \ldots, N \\ \hat{\underline{x}}_k^- - \underline{\Delta}_{(i-N)} & i = n+1, \ldots, 2N \end{cases} \tag{9}$$

Each sigma point is a column vector of length N. To prevent numerical difficulties, we rescale the sigma points as follows:

$$\underline{\chi}^{(i)} = \alpha\underline{\chi}^{(i)} + (1-\alpha)\underline{\chi}^{(0)} \tag{10}$$

Run all the sigma points through the nonlinear predictive system model.

$$\underline{\gamma}^{(i)} = g(\underline{\chi}^{(i)}) \tag{11}$$

Compute an associated set of weighting factors according to $$W^{(i)} = \begin{cases} \frac{\alpha^2 - 1}{\alpha^2} & i = 0 \\ \frac{1}{2N\alpha^2} & i \neq 0 \end{cases} \tag{12}$$

Compute the expected value of the measurement vector.

$$\hat{\underline{y}}_k = \sum_i W^{(i)} \underline{\gamma}^{(i)} \tag{13}$$

Modify the zeroth weighting factor for use in covariance calculations $$W^{(0)} = W^{(0)} + \beta + 1 - \alpha^2 \tag{14}$$

Compute the measurement and cross-covariance matrices.

$$\underline{P}_y = \sum_i W^{(i)}(\underline{\gamma}^{(i)} - \hat{\underline{y}}_k)(\underline{\gamma}^{(i)} - \hat{\underline{y}}_k)^T + \underline{R} \tag{15}$$

$$\underline{P}_{xy} = \sum_i W^{(i)}(\underline{\chi}^{(i)} - \hat{\underline{x}}_k^-)(\underline{\gamma}^{(i)} - \hat{\underline{y}}_k)^T \tag{16}$$

This ends the sigma point estimation step. The covariance of the raw measurements must be estimated, as it must be assumed that the flow equations are non-linear in nature.

The third part of the Kalman prediction step comprises computing $\underline{P}_y^{-1}$ by matrix inversion (its dimension is equal to the number of measurements). Then compute the Kalman gain:

$$\underline{K}_k = \underline{P}_{xy}\underline{P}_y^{-1} \tag{17}$$

When one or more new measurement values are available for time tick k, the Kalman update step begins. The a posteriori state estimate is then computed according to:

$$\hat{\underline{x}}_k^+ = \hat{\underline{x}}_k^- + \underline{K}_k(\underline{y}_k - \hat{\underline{y}}_k) \tag{18}$$

The updated state covariance is:

$$\underline{P}_x^+(k) = \underline{P}_x^-(k) - \underline{K}_k\underline{P}_y\underline{K}_k^T \tag{19}$$

If it is desired to view, or record, filtered measurements, they are given by:

$$\hat{\underline{y}}_k^+ = g(\hat{\underline{x}}_k^+) \tag{20}$$

The state covariance can be propagated as a simple matrix equation (19), because the state transition matrix is linear. The a priori state is estimated using the time-varying state transition matrix shown in FIG. 6, wherein historical and/or periodicity data implicit in the coefficients $\{a_0, \ldots a_n\}$ and $\{b_1, \ldots b_n\}$ can be employed in the estimation.

The unscented transformation is performed on an approximate distribution of data points (x) by a set S of vectors and their associated weights.

The statistics of the transformed set are calculated according to:

$$\hat{\underline{y}}_k = \sum_i W^{(i)} \underline{\gamma}^{(i)} \tag{21}$$

This is the expected value (mean) of the measurement vector. The Kalman update step generates an a posteriori or empirical state estimate ($\hat{\underline{x}}_k^+$) according to equation (18). In addition, the $\underline{P}_x^+$ value must also be computed per equation (19) for use in the next iteration of the Kalman filter.

The empirical state estimate ($\hat{\underline{x}}_k^+$) comprises both measured factors and predicted factors. The a priori or theoretical state estimate ($\hat{\underline{x}}_k^-$) comprises predicted factors based on the history and periodicity of the flow.

The Kalman gain term ($\underline{K}_k$) comprises a gain used to control an amount of change in a subsequent optimized flow measurement(s). The Kalman gain term ($\underline{K}_k$) can be small and therefore can limit the amount of change, such as where the reliability of the unscented Kalman filter is low. Conversely, the Kalman gain term ($\underline{K}_k$) can be large and can allow or force large changes in the resulting optimized measurement(s).

The measurement innovations term ($\underline{y}_k - \hat{\underline{y}}_k^+$) comprises a difference between actual (i.e., empirical) measurements and predicted measurements. It is (typically) a vector whose entries are the prediction error for each empirical (raw) measurement. The measurement innovations term ($\underline{y}_k - \hat{\underline{y}}_k^+$) can vary according to the reliability of the measurement prediction. Consequently, a large measurement innovations term ($\underline{y}_k - \hat{\underline{y}}_k^+$) denotes a large difference between the predicted and actual measurements and therefore a relatively inaccurate measurement prediction. Conversely, a small measurement innovations term ($\underline{y}_k - \hat{\underline{y}}_k^+$) denotes a relatively reliable measurement prediction. Consequently, the ($\underline{x}_k$) term is updated in a manner to compensate for the difference between a previous prediction and actual measurements. At the conclusion of the process, a similar vector can be computed. This is the measurement error vector defined by $\underline{\varepsilon}_k = (\underline{y}_k - \hat{\underline{y}}_k^+)$, where $\hat{\underline{y}}_k^+$ is the vector of "filtered" measurements computed according to equation (20).

Figure 7:
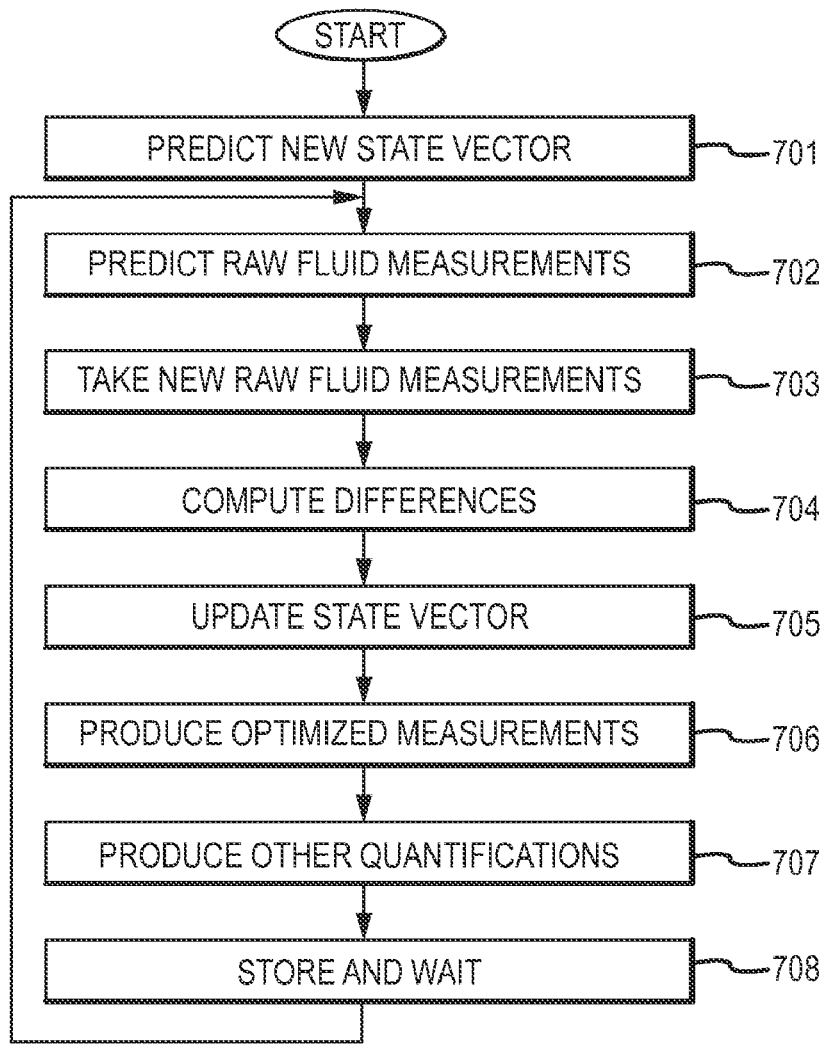
FIG. 7 is a flowchart of a fluid quantification method according to an embodiment of the invention.
Figure 7:

FIG. 7 is a flowchart 700 of a fluid quantification method according to an embodiment of the invention. In step 701, a next state vector is predicted. The predicting may comprise using a predictive system model to generate the predicted next state vector.

In step 702, raw measurement values are predicted. The predicted raw measurement values may be predicted by the unscented Kalman filter using a predictive model based upon previous measurements or historical data. The predicted raw measurements may be predicted from the state vector of step 701.

In step 703, one or more raw fluid measurements are taken. The one or more raw fluid measurements can comprise any desired measurements. In some embodiments, the one or more raw fluid measurements include one or more fluid depth signals and one or more fluid velocity signals. The fluid depth and the fluid velocity can be used to determine a volume flow rate in an open channel, as previously discussed. The one or more raw fluid measurements comprise the raw, substantially unprocessed measurements as they are received from corresponding sensors or measurement devices. However, other measurement signals and/or fluid quantifications are contemplated and are within the scope of the description and claims.

In step 704, the one or more raw fluid measurements are compared to the predicted fluid measurements. The comparison generates error values consisting of the difference between predicted and measured values.

In step 705, the state vector is updated using the error values of step 704. The updating may consist of multiplying the error values by a Kalman gain matrix and adding the result to the predicted state vector of step 701.

In step 706, one or more optimized fluid measurements are produced. The optimized measurements are produced by applying elements of the updated state vector to the latest system model. It should be understood that some parameters of the system model may also reside in the state vector, as can be seen from equations (20) and (5).

The one or more optimized fluid flow measurements do not necessarily correspond and may differ in number from the one or more raw fluid measurements. For example, the one or more raw fluid measurements can comprise a raw fluid depth and a raw fluid velocity, wherein only the raw fluid velocity is optimized and an optimized fluid velocity measurement is subsequently generated. In the matrix given in FIG. 6, the "optimized" result is bulk fluid flow. However, optimized versions of the raw measurements can always be produced, as given in equation (20).

The one or more optimized fluid measurements produced by the unscented Kalman filter offer several advantages. The optimized fluid measurements are typically more accurate than the raw measurements. The optimized fluid measurements may be more accurate than the raw measurements by incorporating a flow periodicity. The optimized fluid measurements can be more accurate than the raw measurements because Kalman filtering fuses information from multiple measurements and sensors. For instance, optimal estimates of fluid velocity and/or level may utilize information from raw measurements of both velocity and level. The processing can identify outliers and errors in the measurements based on one or both of the measurement error $\varepsilon_k$ or the filtered measurements $\hat{y}^+$ and the flow periodicity. The one or more optimized fluid measurements can identify outliers and errors in the measurements and can enable removal or compensation of the outliers and errors. The one or more optimized fluid measurements can identify outliers and errors in the measurements and can enable removal or compensation of the outliers and errors and can use either optimized measurements or historical/periodicity information in substitution. Further, if only one of the raw measurements is suspect, the method can incorporate other raw measurements that are known to be more accurate and reliable. Alternatively, the raw measurements may not be retained at all. Instead, the filtered measurements may be saved for future use.

All or a portion of the raw fluid measurement signals can be optimized, as needed. For example, only fluid variables that tend to inaccuracy or rapid change (or that are otherwise problematic) may be optimized. Alternatively, the method can optimize all measured variables through Kalman filtering, obtaining raw measurements as needed, utilizing the raw measurements that are most reliable, and taking and combining multiple raw measurements from multiple sensors as appropriate.

It should be understood that sensor fusion is inherent in Kalman filtering when more than one sensor (and measurement) is used in the instrument. Sensor fusion is the process of combining of sensor data from multiple sources. Sensor fusion can be performed in a manner such that the resulting information is in some sense better or more accurate and reliable than would be possible when these sensor data sources are used individually.

In some embodiments, the one or more optimized fluid measurements can be used to select and combine the one or more raw fluid measurements and the one or more optimized fluid measurements in predetermined combinations. In some embodiments, the one or more optimized fluid measurements can be used to select and combine the one or more raw fluid measurements and the one or more optimized fluid measurements in predetermined combinations according to a statistical variance of the one or more raw fluid measurements. Again, this inheres in calculating K from $P_y$ and $P_{xy}$ (see equation (18)).

In some embodiments, the estimated system state can be used to select predetermined raw measurements for use in generating the one or more optimized fluid measurements. In some embodiments, the one or more optimized fluid measurements can be used to select predetermined raw measurements for use in generating the one or more fluid quantifications or the appropriate sensor can be energized in order to produce a raw measurement signal. In some embodiments, the one or more optimized fluid measurements can be used to select predetermined raw measurements for use in generating the one or more fluid quantifications and the one or more optimized fluid measurements.

In some embodiments, the optimization can comprise substituting historical, predicted, or filtered measurements for a raw measurement that is an outlier or that is not trusted. Alternatively, the optimization can comprise inserting historical, predicted, or filtered measurements when a sensor measurement has dropped out or is not available for any reason.

In step 707, the one or more optimized fluid measurements are used to generate one or more fluid quantifications. The one or more fluid quantifications do not necessarily correspond in number to the one or more optimized fluid measurements. The one or more fluid quantifications can comprise any manner of fluid or fluid flow characteristics. In some embodiments, the one or more fluid quantifications include a volume flow rate of the fluid, such as in an open channel flow.

It should be understood that selected optimized fluid measurements may be used for generating the one or more fluid quantifications, and not all of the produced optimized fluid measurements may necessarily be used. In addition, selected raw fluid measurements may also be used, as desired, including using none of the raw fluid measurements.

In step 708, the fluid quantifications may be stored. Alternatively, the fluid quantification values may be transmitted to other devices, or used or transmitted in any desired fashion. Further, if desired, the one or more optimized fluid measurements and/or the one or more raw fluid measurements may also be stored and/or transmitted to other devices.

Step 708 may include a wait period, as desired. The wait period may comprise a time interval between raw fluid measurements. The method may then loop back to step 701.

The wait period may comprise part of a power management process. In some embodiments, power consumption is minimized by comparing a statistical variance to a predetermined variance threshold and performing one or more iterations of measurements and subsequent processing. Subsequent measurements and processing could be performed if the statistical variance of ($\underline{x}^+$) or ($\hat{\underline{y}}^+$), for example, exceeds the predetermined variance threshold (or if the error vector $\underline{\varepsilon}_k$ or the innovations ($\underline{y}_k - \hat{\underline{y}}_k$) vector exceed a threshold based on variance). For ($\underline{x}^+$), the comparison would be to the statistical variance, captured in the state covariance matrix $\underline{P}_x$. For ($\hat{\underline{y}}^+$), the comparison could be to the measurement covariance matrix $\underline{P}_y$, but could also be a comparison of ($\underline{y} - \hat{\underline{y}}^-$) or ($\underline{y} - \hat{\underline{y}}^+$) to a threshold, where the threshold might depend on elements of the measurement covariance matrix $\underline{P}_y$. Typically the comparison is to a vector composed of scaled diagonal entries of the chosen covariance matrix. In this manner, as the raw measurements become less predictable and more erratic, the processing of the raw measurements can be increased and an interval between measurements can be correspondingly decreased. Such comparisons are particularly valuable in embodiments wherein the covariance matrices are estimated from incoming data.

In some embodiments, power consumption is minimized by comparing a statistical variance to a predetermined variance threshold and decreasing a measurement interval if the statistical variance exceeds the predetermined variance threshold. A smaller measurement interval generates more data to the unscented Kalman filter, which tracks better as a result. A smaller measurement interval may tend to minimize errors by making outlier or error detection more frequent and accurate.

In some embodiments, power consumption is minimized by comparing an error or a statistical variance to a predetermined variance threshold, measuring a flow characteristic using a lowest power consuming sensor if the statistical variance does not exceed the predetermined variance threshold, and measuring the flow characteristic using a higher power consuming sensor if the statistical variance exceeds the predetermined variance threshold. Alternatively, the power consumption process can compare innovations to a predetermined threshold or can compare error vectors $\underline{\varepsilon}_k$ to a predetermined threshold. The lowest power consuming sensor in some embodiments may be a least accurate sensor, wherein the deficiency in accuracy can be compensated for by employing the processing of the unscented Kalman filter. But mostly what is compensated for by the unscented Kalman filter is the absence of the raw fluid measurements that were skipped or not taken. Conversely, the highest power consuming sensor may be more accurate, but the better accuracy may come at the cost of increased power consumption, wherein such a highest power sensor may be only used as necessary by employing the unscented Kalman filter. In this manner, the accuracy of the measurements and of the fluid quantifications produced from the measurements is increased and controlled, as needed.

Optimal power management can entail turning various sensors on or off as needed, wherein a sensor can be left un-powered if not required. This can be done to reduce power consumption or to reduce wear on sensor having limited service life. When a previously unused sensor becomes needed, it can be powered up in order to generate measurements as needed. Alternatively, a sensor can remain powered and the sensors output can be used or ignored as needed.

The method can be iteratively and/or periodically performed. However, it should be understood that the tracking performed by the unscented Kalman filter enables the method to be performed less often while yet maintaining accuracy and reliability of the fluid quantifications. Moreover, the historical/periodicity information of the unscented Kalman filter can enable the initiation of measurements at predetermined times. This can be employed in order to minimize operation of the flow measurement system and conserve electrical power, for example.

Figure 8:
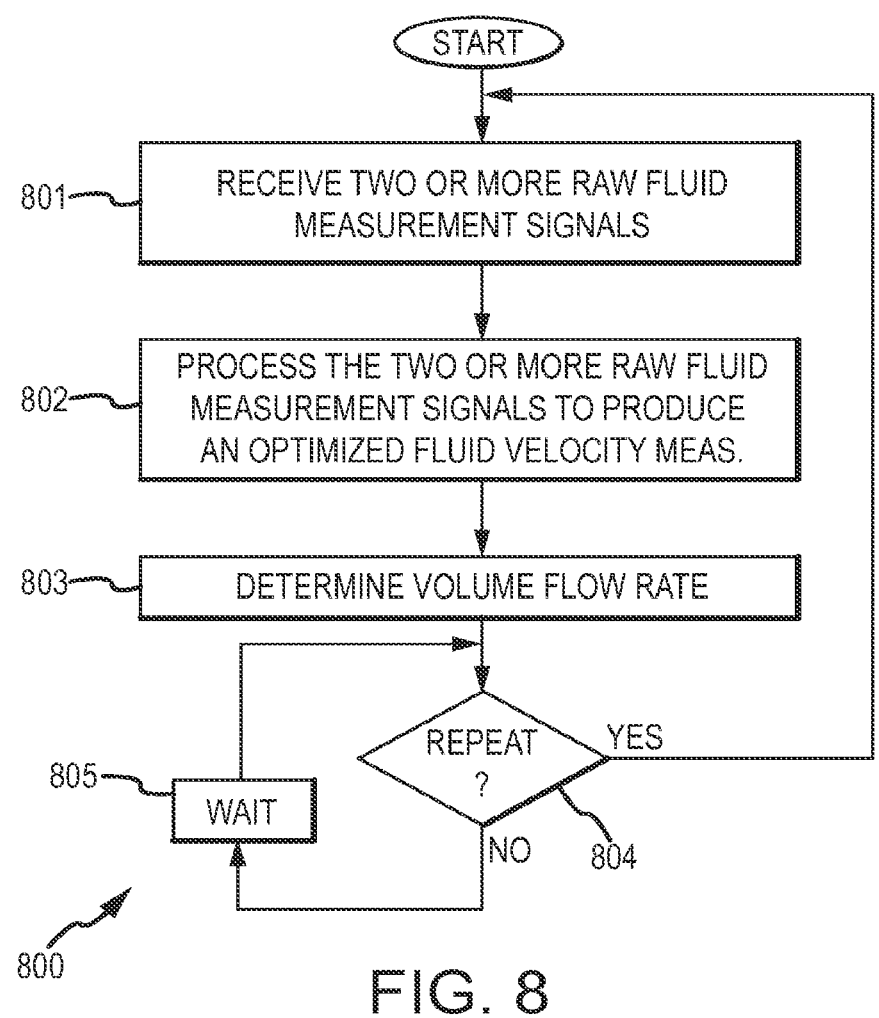
FIG. 8 is a flowchart of a fluid quantification method according to an embodiment of the invention.

FIG. 8 is a flowchart 800 of a fluid quantification method according to an embodiment of the invention. In step 801, two or more raw fluid measurement signals are received. The two or more raw fluid measurement signals can comprise one or more raw fluid depth signals and one or more raw fluid velocity signals.

In step 802, at least one raw fluid measurement is processed with an unscented Kalman filter, as previously discussed. The processing produces at least one optimized fluid measurement, such as an optimized fluid velocity measurement, for example. However, additional raw fluid measurement signals can be processed by the unscented Kalman filter as desired.

In step 803, the at least one optimized fluid measurement is used to determine at least a volume flow rate. For example, at least one optimized fluid velocity measurement can be used in conjunction with a raw or optimized flow depth in order to determine the volume flow rate. Other flow quantifications can be additionally produced.

It should be understood that the sensor fusion process is left out of the description of this flowchart merely for simplicity. The sensor fusion process selects between and combines inputs where the flow meter includes multiple, similar, and/or redundant sensors. The sensor fusion process can schedule measurements. The sensor fusion process can select sensors to be energized or de-energized. The sensor fusion can operate using any number of sensor signals, including a single level measurement and a single velocity measurement.

In step 804, the method checks to determine if it is time for a measurement iteration, as previously discussed. If it is time for a measurement iteration, the method branches back up to step 801. Otherwise, the method branches to step 805 and waits and checks again.

Figure 9:
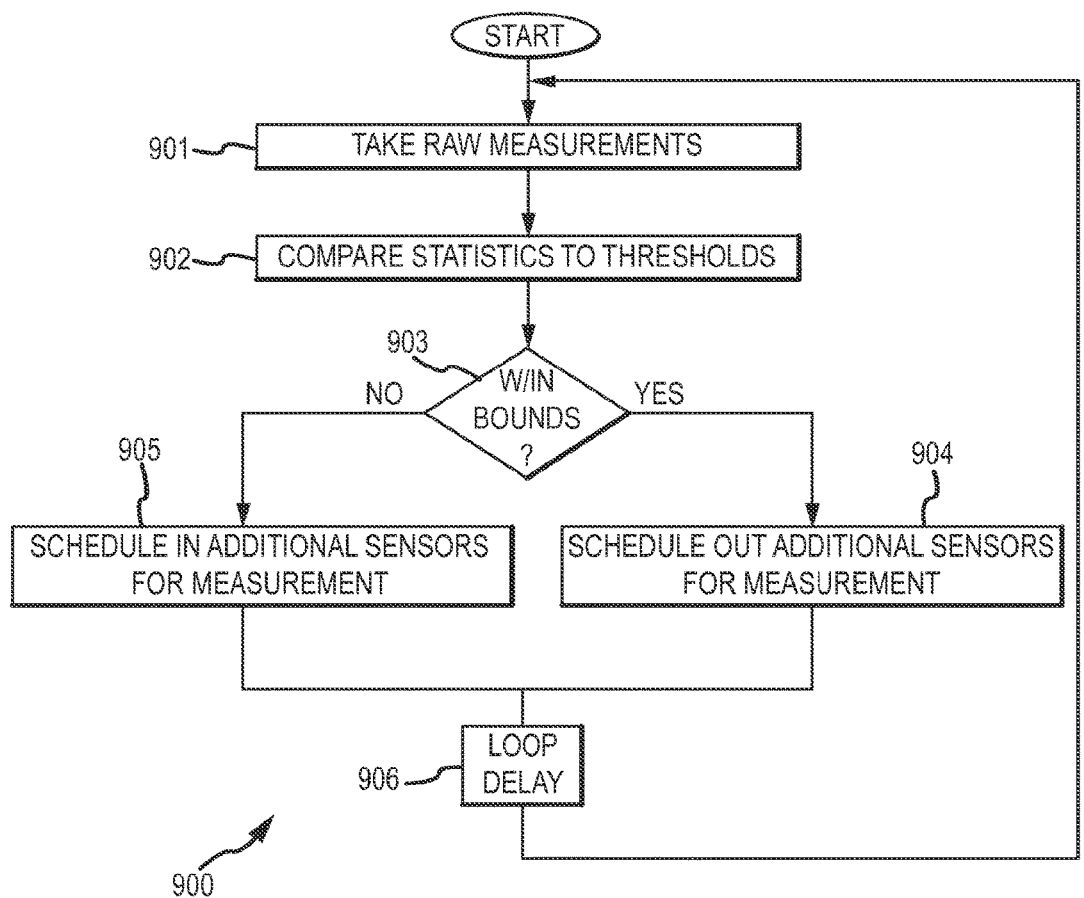
FIG. 9 is a flowchart of a power-saving method according to an embodiment of the invention.

FIG. 9 is a flowchart of a power-saving method according to an embodiment of the invention. The power-saving method advantageously conserves electrical power, such as if the power source is a battery, for example. In step 901, a fluid quantification instrument takes one or more raw fluid measurements of a fluid, as previously discussed.

In step 902, statistics are compared to one or more predetermined thresholds in order to determine if measurement performance is acceptable. For example, a state variance $\underline{P}_x$ may be computed and compared to a state variance threshold. In addition or alternatively, the measurement error or innovations can also be computed and compared to a threshold derived from the sensor measurement matrix $\underline{P}_y$. A test based only on $\underline{P}_y$ will likely indicate that the measurement looks noisy. A test using the error matrix $\underline{\varepsilon}_k$ will likely indicate that the measurement looks incorrect. A test using measurement innovations $(\underline{y}_k - \hat{\underline{y}}_k^+)$ will likely indicate that the measurement looks atypical.

In step 903, if one or both of the state variance $\underline{P}_x$ and the sensor variance $\underline{P}_y$ exceed their thresholds, then operationally the fluid quantification instrument is not operating within bounds. If neither the state variance $\underline{P}_x$ nor the sensor variance $\underline{P}_y$ is out of bounds, then the method proceeds to step 904. Alternatively, if one or both of the state variance $\underline{P}_x$ and the sensor variance $\underline{P}_y$ exceed their thresholds, then the method proceeds to 905.

In step 904, because the fluid quantification instrument is operating within bounds, the current sensors are maintained and no additional sensors are brought on-line or dropped from use. It should be understood that in some embodiments, one or more sensors can be powered down and dropped from use if the fluid quantification instrument is operating within bounds (or has been operating within bounds for a predetermined period of time). Alternatively, there may be another threshold, a too good threshold, wherein if the state variance $\underline{P}_x$ and the sensor variance $\underline{P}_y$ are less than this too good threshold, then sensors may be dropped out, as sensor performance does not require multiple sensors performing the same measurement. After this step, the method loops back up to step 901 and takes further raw measurements. The looping back can include a predetermined delay period.

In step 905, because the fluid quantification instrument is exceeding operational bounds, additional fluid sensors may need to be brought online. For example, if a currently used fluid velocity sensor is exhibiting poor accuracy, then an additional fluid velocity sensor can be powered up used to obtain a different or additional fluid velocity measurement.

In step 906, a predetermined loop delay may be introduced. The predetermined loop delay may achieve a predetermined time period between measurement iterations. The predetermined loop delay may be fixed or variable. The method then loops back to step 901.

Figure 10:
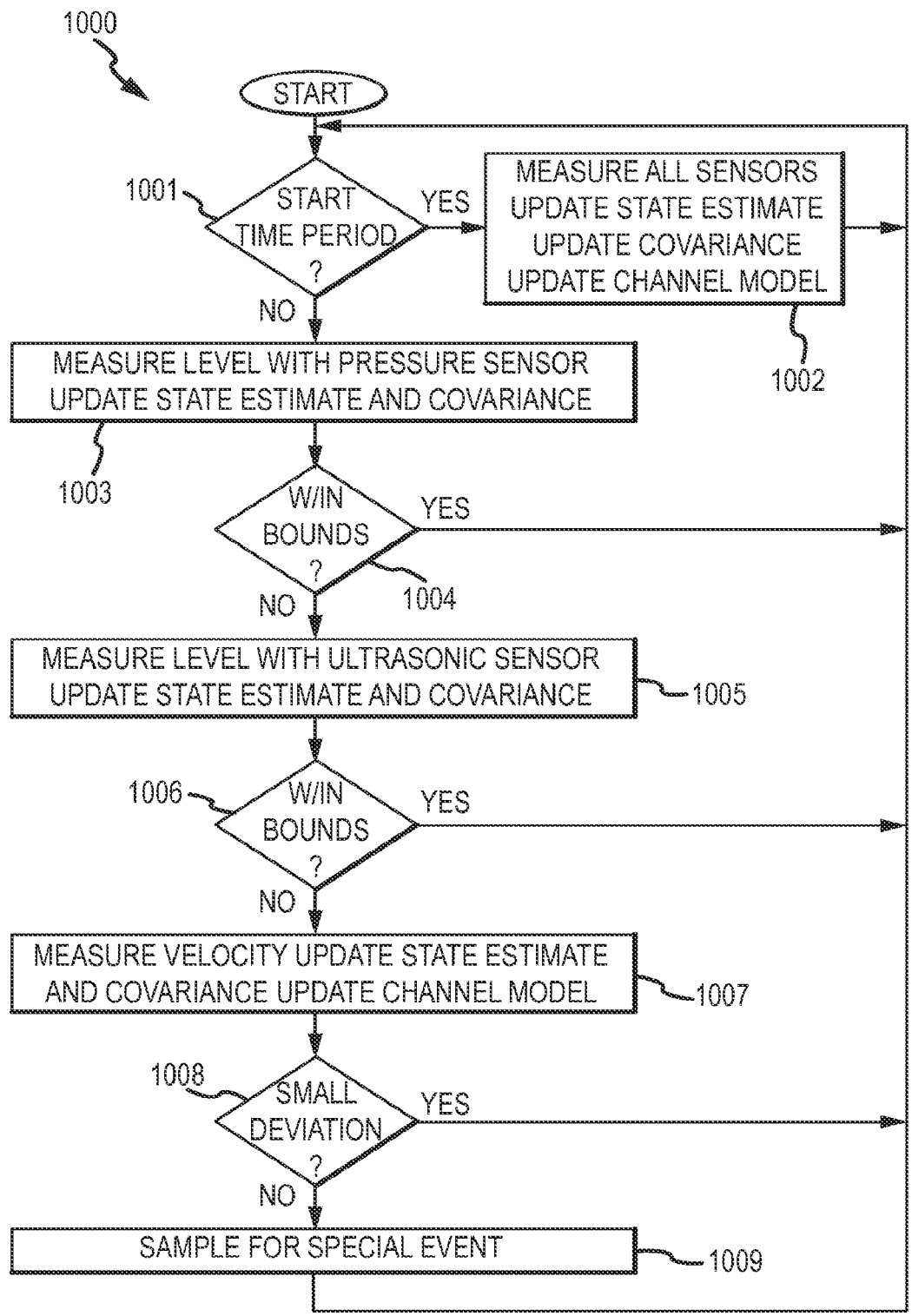
FIG. 10 is a flowchart of a power-saving method according to an embodiment of the invention.

FIG. 10 is a flowchart of a power-saving method according to an embodiment of the invention. In step 1001, a fluid quantification instrument checks to see if a start time period has expired. If the start time period has expired, then the method branches to step 1002. Otherwise, the method proceeds to step 1003.

The start time period can comprise a periodic fluid measurement period, for example. The start time period can comprise a predetermined number of seconds, minutes, or hours. For example, the start time period can comprise an hour and the fluid quantification instrument can perform measurements at least every hour, depending on whether current conditions change or stay the same.

The start time period can be longer that the main loop time of the fluid quantification instrument. The start time period can be chosen to generate useful fluid quantifications while yet minimizing operational power consumption, for example. In some embodiments, the fluid quantification instrument can be woken up when the start time period has expired, perform measurements and calculations as desired, and then the fluid quantification instrument can go back into a sleep mode until a next start time period expiration.

In step 1002, measurements are obtained from all sensors. This can include obtaining measurements from sensors having varying levels of accuracy and reliability. This can include obtaining measurements from sensors having varying levels of power consumption. After the measurements are obtained, the method processes the new measurements and updates the state estimate, the covariance, and the channel model. The state estimate, the covariance, and the channel model are now up to date and reflect current fluid conditions/current flow conditions. At the end of this step, the method loops back to step 1001.

In step 1003, where the start time period has not yet expired, the method measures a fluid level with a pressure sensor. The pressure sensor typically requires a low amount of electrical power and therefore may be employed more often than other level sensors, such as an ultrasonic fluid level sensor. After the level measurement is obtained, the state estimate and covariance are again updated in order to reflect current conditions.

In step 1004, the state estimate and covariance are compared to thresholds in order to determine if the pressure sensor level measurement is within predetermined acceptable bounds. If the pressure sensor level measurement is within predetermined acceptable bounds, then the method loops back to step 1001. Otherwise, where the pressure sensor level measurement is not within predetermined acceptable bounds, the method proceeds on to step 1005.

In step 1005, the method measures the fluid level with an ultrasonic sensor. The ultrasonic level sensor may be more accurate and reliable than the pressure level sensor, but may consume more electrical power. Here, where the pressure sensor level measurement has been determined to be lacking due to some test result, then the ultrasonic level sensor is employed. As before, the state estimate and covariance are updated to reflect current conditions. The updating will capture the deviations within the state estimate and covariance.

In step 1006, the newly updated state estimate and covariance are again compared to thresholds in order to determine if the ultrasonic sensor level measurement is within predetermined acceptable bounds. If the ultrasonic sensor level measurement is within predetermined acceptable bounds, then the method loops back to step 1001. Otherwise, where the ultrasonic sensor level measurement is not within predetermined acceptable bounds, the method proceeds on to step 1007.

In step 1007, the method measures fluid flow velocity. Here, where the both the pressure and ultrasonic sensors indicate that one or both of the state estimate and covariance are deviating too much, then the velocity sensor is employed. If the state estimate and covariance are deviating, then the method does not wait for the start time period to expire before measuring fluid velocity again. The velocity sensor can, for instance, measure a point velocity in the fluid flow. The meter electronics can process the point velocity in order to obtain or estimate an average fluid velocity. Subsequently, the state estimate and covariance are again updated to reflect current conditions. The updating will capture the deviations within the state estimate and covariance.

In step 1008, the deviations within the state estimate and covariance are compared to a deviation threshold in order to determine the magnitude of the deviations. If the deviations do not exceed the deviation threshold, then the deviations are small and the method loops back to step 1001. Consequently, the method determines that the measurements performed in steps 1003, 1005, and 1007 are adequate to fully quantify the fluid and/or fluid flow. Otherwise, where the deviations exceed the deviation threshold, then the deviations are not small and the method proceeds on to step 1009.

In step 1009, the method judges the deviations in the state estimate and covariance to be significant and generates an indication to sample for a special event. For example, the indication can comprise a signal to sample for or obtain information related to a recent rainfall. The indication in some embodiments can request additional measurements or information from external devices. The indication in some embodiments can signal the likely occurrence of a special event. The indication can be transferred to an operator or other monitoring system. The indication in some embodiments can trigger further sensors to be brought online. At the end of the sample or indication, the method loops back to step 1001. In steps 1003, 1005, 1007, the updates are based on individual measurements, and so the matrix equations given herein are partitioned to reduce the measurement dimensionally. The method of doing this is called "sequential update."

One advantage of the fluid quantification instrument and method is the ability in some embodiments to process measurements that may include noise, errors, or other unwanted variations and yet generate more accurate and reliable results.

Another advantage of the fluid quantification instrument and method is the ability in some embodiments to detect spikes, drop-outs, or other outliers, irregularities, or errors in measurements. Such errors can contribute much inaccuracy to the measurements. The identified irregularities can be omitted from or compensated for in the measurement results, can dictate the retaking of measurements, can give a user an indication of the reliability of the end results, etc. Further, identification of measurement irregularities can also be used to increase a measurement rate, generate an alarm to a user or operator, or trigger an automated sampler device, among other things.

Another advantage of the fluid quantification instrument and method is the ability in some embodiments to detect and mitigate (or replace) a spike or outlier with a reliable estimate of the proper value. Another advantage of the fluid quantification instrument and method is the ability in some embodiments to replace a drop-out in a measurement with a predicted or estimated value that is based on historical measurement data, including historical data that captures a periodicity in the measurements. Alternatively, the replacement can be accomplished with measurement data from other sensors that did not drop out. In most cases, the replacement will be made on the basis of both the history/periodicity and the measurement data from other sensors.

I claim:

1. A fluid quantification instrument, comprising:
one or more sensor probes; and
meter electronics in communication with the one or more sensor probes, with the meter electronics being configured to:
receive one or more raw fluid measurements from the one or more sensor probes;
process the one or more raw fluid measurements using a predictive system model to produce one or more optimized fluid measurements, wherein to produce the one or more optimized fluid measurements comprise filtering the one or more raw fluid measurements by selecting a set of sample points from the one or more raw fluid measurements and using the selected set of sample points to capture a mean and covariance of an output of the processing, wherein to process comprises comparing the one or more raw fluid measurements to at least one fluid measurement predicted using the predictive system model to generate at least one error value and comparing the at least one error value to an error value threshold;
automatically managing power consumed by the fluid quantification instrument by adjusting a fluid measurement interval based upon the comparison of the at least one error value to an error value threshold, wherein the adjusting comprises decreasing the fluid measurement interval if the at least one error value is greater than the error value threshold; and
determine one or more fluid quantifications using at least the one or more optimized fluid measurements, wherein the one or more fluid quantifications comprise a fluid measurement indirectly measured via calculation from the one or more optimized fluid measurements.

2. The fluid quantification instrument of claim 1, with the predictive system model being provided by an unscented Kalman filter.

3. The fluid quantification instrument of claim 1, with the one or more raw fluid measurements including at least a raw fluid depth measurement signal and a raw fluid velocity measurement signal that are used to determine a volume flow rate of the fluid.

4. The fluid quantification instrument of claim 1, with the meter electronics being further configured to generate a plurality of Fourier coefficients related to a flow state periodicity.

5. The fluid quantification instrument of claim 1, with the meter electronics being further configured to generate a plurality of Fourier coefficients related to a periodicity in one or more elements of a state vector.

6. The fluid quantification instrument of claim 1, further comprising:
comparing one or more elements of the predictive system model to one or more corresponding thresholds; and
performing one or more optimization actions if the one or more elements do not satisfy the one or more corresponding thresholds.

7. The fluid quantification instrument of claim 6, with the one or more elements of the predictive system model comprising a predicted measurement error $|(y_k - \hat{y}_k^-)|$ that is compared to predetermined scaled elements of the sensor covariance matrix (Py), an estimated measurement error $|(y_k - \hat{y}_k^+)|$ that is compared to predetermined scaled elements of the sensor covariance matrix (Py), or an estimated state error $|(\hat{x}_k^+ - \hat{x}_k^-)|$ that is compared to predetermined scaled elements of the state covariance matrix (Px).

8. The fluid quantification instrument of claim 6, with performing one or more optimization actions comprising decreasing a measurement interval if the one or more elements of the predictive system model do not satisfy the one or more corresponding thresholds.

9. The fluid quantification instrument of claim 6, with performing one or more optimization actions comprising determining a future timing of one or more predetermined raw measurements based on the one or more elements of the predictive system model or selecting one or more predetermined sensors to use based on the one or more elements of the predictive system model in order to affect power consumption of the fluid quantification instrument.

10. The fluid quantification instrument of claim 1, wherein a predetermined optimized fluid measurement is obtained by combining two or more predetermined raw fluid measurements through statistical sensor fusion.

11. A fluid quantification method, comprising:
receiving, using one or more sensor probes of a fluid quantification instrument, one or more raw fluid measurements;
processing, using meter electronics of the fluid quantification instrument, the one or more raw fluid measurements using a predictive system model to produce one or more optimized fluid measurements, wherein to produce the one or more optimized fluid measurements comprise filtering the one or more raw fluid measurements by selecting a set of sample points from the one or more raw fluid measurements and using the selected set of sample points to capture a mean and covariance of an output of the processing, wherein the processing comprises comparing the one or more raw fluid measurements to at least one fluid measurement predicted using the predictive system model to generate at least one error value and comparing the at least one error value to an error value threshold;
automatically managing power consumed by the fluid quantification instrument by adjusting a fluid measurement interval based upon the comparison of the at least one error value to an error value threshold, wherein the adjusting comprises decreasing the fluid measurement interval if the at least one error value is greater than the error value threshold; and
determining, using the meter electronics of the fluid quantification instrument, one or more fluid quantifications using at least the one or more optimized fluid measurements, wherein the one or more fluid quantifications comprise a fluid measurement indirectly measured via calculation from the one or more optimized fluid measurements.

12. The method of claim 11, with the predictive system model being provided by an unscented Kalman filter.

13. The method of claim 11, with the one or more raw fluid measurements including at least a raw fluid depth measurement signal and a raw fluid velocity measurement signal that are used to determine a volume flow rate of the fluid flow.

14. The method of claim 11, further comprising generating a plurality of Fourier coefficients related to a flow state periodicity.

15. The method of claim 11, further comprising generating a plurality of Fourier coefficients related to a periodicity in one or more elements of a state vector.

16. The method of claim 11, further comprising:
comparing one or more elements of the predictive system model to one or more corresponding thresholds; and
performing one or more optimization actions if the one or more elements do not satisfy the one or more corresponding thresholds.

17. The method of claim 16, with the one or more elements of the predictive system model comprising a predicted measurement error $|(y_k-\hat{y}_k^-)|$ that is compared to predetermined scaled elements of the sensor covariance matrix (Py), an estimated measurement error $|(y_k-\hat{y}_k^+)|$ that is compared to predetermined scaled elements of the sensor covariance matrix (Py), or an estimated state error $|(\hat{x}_k^+-\hat{x}_k^-)|$ that is compared to predetermined scaled elements of the state covariance matrix (Px).

18. The method of claim 16, with performing one or more optimization actions comprising decreasing a measurement interval if the one or more elements of the predictive system model do not satisfy the one or more corresponding thresholds.

19. The method of claim 16, with performing one or more optimization actions comprising determining a future timing of one or more predetermined raw measurements based on the one or more elements of the predictive system model or selecting one or more predetermined sensors to use based on the one or more elements of the predictive system model in order to affect power consumption.

20. The method of claim 11, wherein a predetermined optimized fluid measurement is obtained by combining two or more predetermined raw fluid measurements through statistical sensor fusion.

\* \* \* \* \*